United States Patent [19]

Butelman et al.

[11] Patent Number: 5,225,529
[45] Date of Patent: Jul. 6, 1993

[54] SYNTHETIC AMPHIPHILIC GLYCOCONJUGATES FOR NEUROLOGICAL USE

[75] Inventors: Edoardo Butelman; Cesare Sirtori, both of Milan, Italy

[73] Assignee: Farmhispania S.A., Barcelona, Spain

[21] Appl. No.: 471,525

[22] Filed: Jan. 29, 1990

[30] Foreign Application Priority Data

Jan. 30, 1989 [IT] Italy ............................. 19241 A/89

[51] Int. Cl.⁵ ............... C07H 13/04; A61K 37/02; C07K 9/00
[52] U.S. Cl. .................. 530/322; 530/331; 530/399; 536/17.2; 536/17.9; 536/18.7; 536/116; 536/119
[58] Field of Search .............. 536/119, 4.1, 17.2, 536/17.9, 18.7, 116, 126; 530/322, 331, 395, 399

[56] References Cited

U.S. PATENT DOCUMENTS 3,947,352  3/1976  Cuatrecasas et al. ............. 530/395
4,719,202  1/1988  Van Boeckel et al. ............. 514/53

OTHER PUBLICATIONS

Morrison & Boyd "Organic Chemistry", published 1975 by Allyn and Bacon, Inc. (Boston), see p. 585.

*Primary Examiner*—Johnnie R. Brown
*Assistant Examiner*—Everett White
*Attorney, Agent, or Firm*—Birch, Stewart, Kolasch & Birch

[57] ABSTRACT

Chemically and sterically pure synthetic amphiphilic glycoconjugates for neurological use of the formula (I):

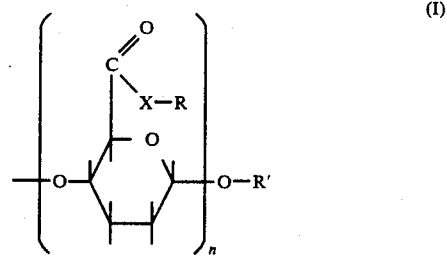

in which:
the saccharide ring represents a monosaccharide such as glucose, galactose or mannose;
X represents O or NH and, when X represents O, R is a choline radical whereas, when X represents NH, R is an amino acid or peptide radical; R' represents a saturated or unsaturated linear or branched $C_8$–$C_{18}$ aliphatic chain, or a

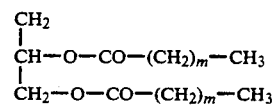

group or a

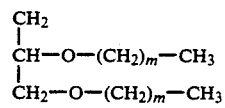

group where m is between 7 and 17 and;
n is a whole number from 1 to 5.

11 Claims, No Drawings

SYNTHETIC AMPHIPHILIC GLYCOCONJUGATES FOR NEUROLOGICAL USE

FIELD OF THE INVENTION

This invention relates to compounds for use in the treatment of diseases of the central nervous system.

PRIOR ART

Neurological diseases, and in particular those relating to degeneration of the central nervous system with progressive loss of memory and the ability to recognise, represent a medical and social problem of increasing importance, especially in the western world. In particular, Alzheimer's disease is prevalent in 0.8% of the 65 year old population and increases rapidly beyond 65 years.

One of the most important events occurring during the course of degenerative diseases of the central nervous system is insufficiency in the synthesis and pickup of pharmacodynamically active neuro-transmitters, particularly of amino acid and peptide structure (Bowen et al. in Brain, 99, 459–496, 1976).

It has been proposed to use natural glycolipids to correct irregularities in the transmembrane nervous transmission mechanisms in these diseases (Mamoli et al., Eur. Neurol., 19, 320–326, 1980).

However, glycolipids have the drawback of being poorly specific and having relatively low pharmacodynamic activity. In this respect, they are active only in relatively high doses and act by various mechanisms.

There is therefore the problem of finding substances having greater activity and specificity in the treatment of said diseases, and possibly suitable for parenteral administration.

SUMMARY OF THE INVENTION

We have now discovered new compounds which allow considerable improvement in the treatment of neurological diseases, particularly of diseases which result in degeneration of the central nervous system.

Said compounds consist of chemically and sterically pure synthetic amphiphilic glycoconjugates of the formula (I):

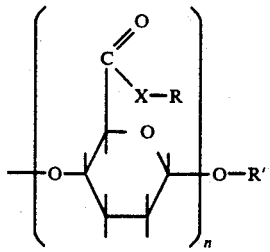
(I)

in which:
the saccharide ring represents a monosaccharide such as glucose, galactose or mannose;
X represents O or NH and, when X represents O, R is a choline radical whereas, when X represents NH, R is an amino acid or peptide radical; R' represents a saturated or unsaturated linear or branched $C_8$–$C_{18}$ aliphatic chain, or a

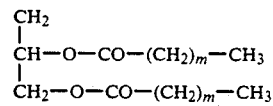

group or a

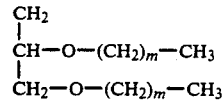

group where m is between 7 and 17;
n is a whole number from 1 to 5.

The compounds of the present invention are prepared using a process in which:

a) a compound of general formula (II)

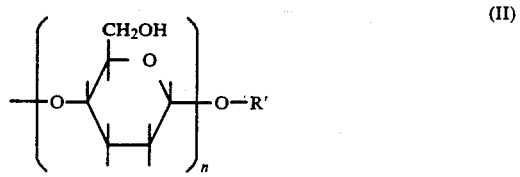
(II)

is treated with an oxidizing agent to obtain the corresponding carboxylic acid;

b) the carboxylic acid obtained in stage a), or a derivative thereof of activated ester type, is reacted with choline or with an amino acid or with a peptide to obtain the compound (I).

DETAILED DESCRIPTION OF THE INVENTION

The characteristics and advantages of the amphiphilic glycoconjugates for neurological use according to the present invention and their preparation process will be more apparent from the following detailed description.

The compounds of the invention are prepared by way of intermediate compounds of the formula (II)

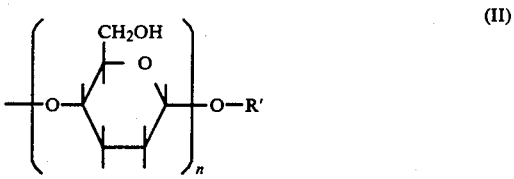
(II)

in which:
the saccharide ring represents glucose, galactose or mannose;
R' represents a saturated, unsaturated linear or branched $C_8$–$C_{18}$ aliphatic chain, or a

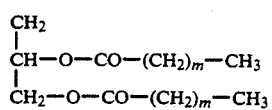

group or a

-continued

CH₂
|
CH—O—(CH₂)ₘ—CH₃
|
CH₂—O—(CH₂)ₘ—CH₃ group where m is between 7 and 17;
n is a whole number from 1 to 5.

The intermediate compounds (II) are prepared from commercially available raw materials by a series of reactions known in the chemical preparation art.

The primary hydroxyl of the compound (II) is then selectively oxidized to a carboxyl group by treatment with an oxidizing agent in a reaction medium consisting of an organic solvent.

The organic solvent is preferably acetone, in which the compound (II) is dissolved in a quantity of between 40 and 60 g/l. The preferred oxidizing agent is CrO₃ in H₂SO₄ of between 3 and 4M.

The quantity of CrO₃ used is between 0.8 and 1.2 g/g of (II) and the quantity of H₂SO₄ used is between 2.5 and 3 ml/g of CrO₃. Other oxidizing agents which can be used are potassium permanganate and nitric acid.

The oxidizing agent is mixed with the compound (II) at 0° C. under stirring.

The first reaction stage, lasting 5-15 minutes, is carried out under stirring while cooling to 0° C., and the second reaction stage, lasting 50-100 minutes, is carried out by suspending the cooling but continuing the stirring.

The product is isolated in the pure state by normal separation and purification techniques.

The carboxylic acid of formula (III) is obtained:

(III)

From the obtained carboxylic acid, or from an ester derived therefrom, the compound of the formula (I)

(I)

is prepared in which:

X represents O or NH and, when X is O, R is a choline radical whereas, when X is NH, R is an amino acid or peptide radical.

To prepare the compound (I) in which X represents O, the carboxylic acid (III) is treated with choline in an organic solvent in the presence of a condensing agent.

Preferably, said organic solvent is DMF and said condensing agent is N,N-dicyclohexylcarbodiimide (DCC), the reaction being conducted at ambient temperature under stirring for 15-20 hours.

The molar ratio of the carboxyl derivative to the choline used for the reaction is between 1.0 and 5.0.

The product (I) obtained is isolated from the reaction mixture and purified by the usual separation and purification methods.

To prepare compounds (I) in which X represents NH, the carboxylic acid (III) is treated with an amino acid or a peptide in an aqueous environment in the presence of a condensing agent.

The reaction is preferably conducted in water or in a pH 4-5 buffered solution in the presence of N-ethyl-N-dimethylaminopropylcarbodiimide at a temperature of between 15° and 35° C., under stirring, for 2-24 hours.

The molar ratio of the carboxyl derivative to the amino acid or peptide used for the reaction is between 1.0 and 3.0.

The product (I) obtained is isolated from the reaction mixture and purified by the usual separation and purification methods.

Amino acids and peptides which can be used for obtaining the compounds (I) according to the present invention include: glycine, glutamic acid, Me-D-aspartate, L-pyroglutamyl-L-histidyl-L-proline, γ-amino-β-hydroxybutyric acid, hydroxytryptophan, MSH/ACTH (melanocyte stimulating hormone/adrenocorticotropin), ACTH, 1-desamino-8-D-arginine-vasopressin, S-adenosylmethionine.

The following examples of the preparation of compounds according to the invention are given by way of non-limiting illustration only.

EXAMPLE 1

Preparation of
1-O-(6-O-choline)-β-D-dodecylglycopyranosiduronic ester (ACG-choline)

a) Preparation of 1-0-β-D-dodecylglucopyranoside
50 ml (415 mmoles) of trichloroacetylnitrile are added to a solution containing 50 g (92.5 mmoles) of 2,3,4,6-tetra-O-benzylglucose in 500 ml of absolute CH₂Cl₂ at 25° C. under stirring. 4.0 g (168 mmoles) of NaH are then added gradually. The reaction is conducted for 6 hours at 25° C., the solution then being concentrated under vacuum and filtered through silica gel.

A light oil is obtained which crystallizes spontaneously with a yield of 90%.

The product is dissolved in 200 ml of absolute CH₂Cl₂ and 10 ml (64 mmoles) of dodecanol, and the solution is cooled to −20° C.

A 0.4M solution of BF₃ in Et₂O is added, and after one hour at ambient temperature the reaction mixture is treated with NaHCO₃, washed with water and dried with anhydrous Na₂SO₄.

An oily product is obtained which on silica gel flash-chromatography gives 48 g of 1-0-dodecyl-2,3,4,6-tetra-O-benzyl-β-D-glucopyranoside, which is debenzylated in an H₂ atmosphere over Pd-C catalyst containing 10 weight % of Pd.

The filtrate is then evaporated and subjected to silica gel chromatography in EtOAc:MeOH (6:1) to obtain, with quantitative yield, chemically and sterically pure 1-0-β-D-dodecylglucopyranoside of formula (IV)

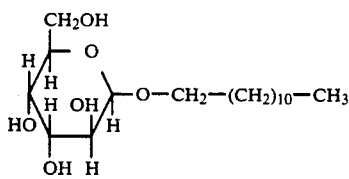

(IV)

On 'HNMR analysis the anomeric configuration of (IV) was found to be exclusively of β type.

b) Selective oxidation of the primary hydroxyl.

A solution of 1 g of CrO$_3$ in 2.7 ml of 3.5M sulphuric acid is added to a solution of compound (IV) in acetone (1 g/20 ml) under agitation at 0° C.

Cooling is suspended after 10 minutes and the mixture is stirred for a further 60 minutes and then filtered through a sintered glass filter on crushed ice.

The solid is washed with acetone and the mixture consisting of the filtrate and the wash liquid is concentrated, the aqueous phase being washed with chloroform, dried with Na$_2$SO$_4$, evaporated to dryness, methanol added and the solution fed to a column of Amberlite IRA-402(OH$^-$) and eluted with methanol to eliminate the unreacted material and the oxidation by-products.

The carboxylic acid derivative is obtained by elution with methanol/acetic acid/water (45:45:10) and evaporated to dryness.

It corresponds to the formula (V):

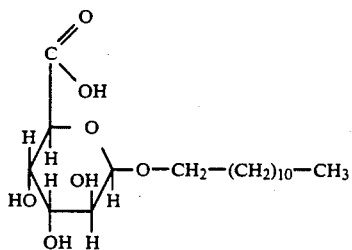

(V)

c) Esterification of the product (V) with choline 5 g of (V) are treated with 2 g of choline in 20 ml of DMF in the presence of 2.9 g of N,N-dicyclohexylcarbodiimide (DCC) at ambient temperature under stirring for 16 hours.

The mixture is diluted with water and centrifuged to remove the dicyclohexylurea.

The mixture is then evaporated to dryness and purified by silica gel flash-chromatography using ethyl acetate as eluent.

The solvent is evaporated and the product recrystallized three times from ethyl acetate.

5.13 g of the product AGC-choline are obtained, of formula (VI)

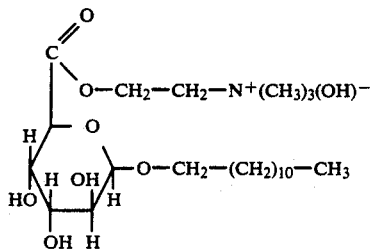

(VI)

Analysis: Calculated: C=59.93%, H=10.17%, N=3.11%; Found: C=59.81%, H=10.01%, N=3.10%.

EXAMPLE 2

Preparation of 1,2-di-octadecanoyl-3-O-[4-O-α-D-glucoronyl GABOB(1-4)glucoronyl GABOB]-L-glycerol a) Preparation of 1,2-di-O-octadecanoyl-3-O-[4-O-(α-D-glucopyranosyl)β-D-glucopyranosyl]-L-glycerol.

9.7 g of 1,2-O-isopropylidene-L-glycerol are transformed into allyl ether, of which 13.7 g are treated with 190 ml of methanol and 10 ml of 1N H$_2$SO$_4$ under reflux for 15 minutes to obtain complete conversion into 3-O-allyl-L-glycerol (8.8 g), which is treated with 20 ml of benzyl chloride and 5 g of NaH in tetrahydrofuran under reflux for 6 hours.

The product is isolated and treated with potassium-t-butoxide in DMSO at 60° C.

The new product is isolated and treated with HgCl$_2$ and HgO and the mixture is chromatographed on alumina to obtain 13.4 g of 1,2 di-O-benzyl-L-glycerol, which is characterized as a tritylic ether (M.P. 84° C., [α]$_D$=+8.0, C=1 in CHCl$_3$), The 1,2 di-O-benzyl-L-glycerol is treated with heptaacetylmaltose bromide in 100 ml of anhydrous benzene-nitromethane (1:1) mixture in the presence of 5 g of Hg(CN)$_2$.

The mixture is washed with water and then with an NaHCO$_3$ solution and water, and dried with Na$_2$SO$_4$.

The crude product is purified by silica gel flash-chromatography using diethylether-ethylacetate (10:1) as eluent.

100 ml of methanol are added to the product and the mixture treated with H$_2$ on a Pd/C catalyst with 10% by weight Pd, and then filtered to obtain 10 g of 3-O-[4-O-(α-D-glucopyranosyl)-β-D-glucopyranosyl] L-glycerol.

A solution of this product in 100 ml of anhydrous pyridine and 25 ml of octadecanoylchloride is kept at 20° C. for 16 hours and the product obtained is isolated by silica gel flash chromatography using as eluent a 1:1 toluene:ether mixture to obtain 12 g of 1,2-di-O-octadecanoyl-3-O-[4-O-(α-D-glucopyranosyl)β-D-glucopyranosyl]-L-glycerol of formula (VII):

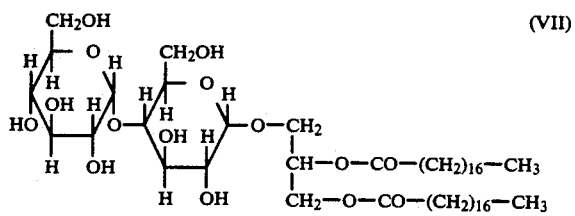

(VII)

b) Selective oxidation of the primary hydroxyl.

The compound (VII) (15 g) is oxidized to obtain the corresponding carboxyl derivative. The oxidation is conducted with CrO$_3$—H$_2$SO$_4$ in acetone at 0° C. using the method described under point b) of Example 1.

11.3 g of 1,2-di-O-octadecanoyl-3-O-[4-O-(α-D-glucopyranouronyl)β-D-glucopyranouronyl]-L-glycerol are obtained corresponding to formula (VIII):

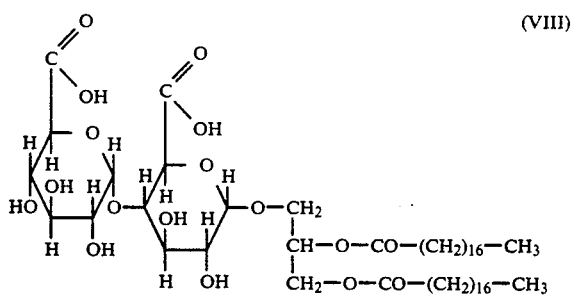

(VIII)

c) Amidation of the compound (VIII) with the methyl ester of γ-amino-β-hydroxybutyric acid (GABOB).

The compound (VIII) is treated with 1.83 g of GABOB methylester in an aqueous environment in the presence of 2.36 g of N-ethyl-N-dimethylaminopropyl-carbodiimide at pH 4.5 at a temperature of 0° C. for 2 hours and then at ambient temperature for 16 hours.

The mixture is centrifuged, extracted with chloroform, dried with anhydrous $Na_2SO_4$ and filtered, the product being recovered by evaporating the solvent.

The ester bond is eliminated by treatment with potassium peroxide in the presence of 18-crown-6 ether in benzene at ambient temperature for 24 hours.

The mixture is filtered through celite, the solvent is removed by evaporation and the product crystallized three times from 5:1 $CHCl_3$:MeOH.

9.5 g of the product AGC-GABOB are obtained, corresponding to formula (IX):

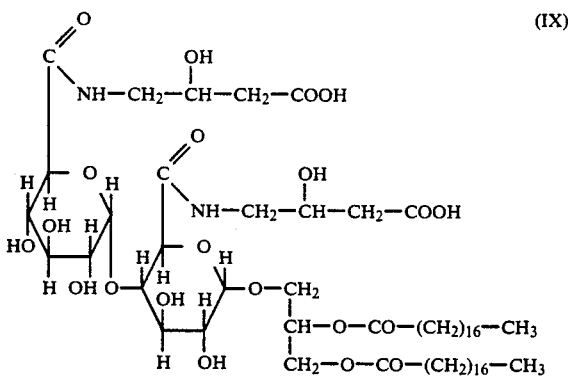

(IX)

Analysis: Calculated: C=59.98%, H=9.21%, N=2.36%; Found: C=59.61%, H=9.15%, N=2.25%.

EXAMPLE 3

The compound (VIII) of Example 2 (30 g) is dissolved in 100 ml of DMF and 5 g of N,N'-carbonyldiimidazole are added to the solution in small doses at ambient temperature. When effervescence ceases, the reaction mixture is heated to 60° C. and maintained at this temperature for 2 hours.

A three times excess of GABOB methylester is added to the solution and the mixture is kept at 70° C. for 16 hours.

The reaction product is poured into a mixture of ice and water, followed by extraction with $CHCl_3$ and silica gel purification (eluent $EtOAc-Et_2O$ 3:1) to obtain the product (IX) with a yield of 61%.

Pharmacological trials

Numerous trials on different animal models were carried out to evaluate the therapeutic activity of the compounds according to the invention in the neurological field. The methods of operation and the results obtained are reported hereinafter and in the accompanying tables.

1. Increase in the cerebral content of acetylcholine (ACh) following administration of choline (Ch) or AGC-choline (Compound VI)

The trial was carried out by the method described by Hirsch and Wurtman (Science, 202, 223–225, 1978).

Choline and compound (VI) were administered intraperitoneally to Sprague Dawley rats weighing 150–250 g, the Ch and ACh content being determined in the cerebral cortex of the rats at intervals as described by Jope (J. Pharmacol. Exp. Ther. 1220, 322–326, 1982).

The trial was conducted on 80 male rats. Ten rats were killed immediately to determine the initial Ch and ACh concentration in the cerebral cortex.

The remaining 70 rats were divided into two groups, to one of which Ch was administered intraperitoneally at a dose of 100 mg/kg, and to the other of which compound (VI) was administered by the same method and at the same dose as the Ch.

Five rats of each group were killed at 30 mins, 60 mins, 2 h, 4 h, 8 h 12 h and 24 h after the administration, their cerebral cortices being sectioned and the cortical ACh and Ch contents determined.

The results are reported in Table 1, from which it can be seen that administering Ch in no case leads to statistically significant changes in ACh content whereas the Ch content increases by approximately 40% 1 h and 2 h after administration.

In contrast, administering the compound (VI) results in remarkable increases in ACh, which increases by between 20 and 40% during the period extending from one hour to 12 hours after administration, with no content variations after 24 hours. In addition, administration of compound (VI) results in considerable Ch increases for prolonged times, noted even 24 hours after administration.

These results indicate significant differences between the metabolic behaviour of Ch and compound (VI). In particular, whereas Ch acts to induce only a temporary increase of cortical Ch, compound (VI) is more effective in increasing Ch content and in inducing a prolonged ACh increase.

TABLE 1

Choline (Ch) and acetylcholine (ACh) levels in the cerebral cortex of rats after i.p. administration of choline (100 mg/kg) or AGC-choline (equivalent dose) (5 rats per experiment, nmol/g, $\bar{X} \pm MSE$)

| | Choline | | AGC-choline | |
|---|---|---|---|---|
| Time | Ch | ACh | Ch | ACh |
| 0 | 18.2 ± 2.1 | 17.0 ± 0.7 | 17.6 ± 1.5 | 16.4 ± 0.9 |
| 30 min | 20.7 ± 1.6 | 18.2 ± 1.4 | 30.5 ± 3.4** | 24.7 ± 1.9** |
| 60 min | 22.4 ± 2.9* | 17.8 ± 1.5 | 36.7 ± 4.7*** | 26.2 ± 2.4*** |
| 2 h | 23.1 ± 3.5** | 17.4 ± 0.9 | 37.5 ± 3.9*** | 23.9 ± 2.0** |
| 4 h | 22.0 ± 2.2* | 17.9 ± 1.4 | 39.6 ± 5.7*** | 21.5 ± 1.4** |
| 8 h | 19.5 ± 1.4 | 17.5 ± 1.1 | 30.3 ± 4.4** | 20.3 ± 0.8 |
| 12 h | 17.6 ± 0.7 | 18.0 ± 0.9 | 18.1 ± 1.4 | 19.6 ± 0.5* |

TABLE 1-continued

Choline (Ch) and acetylcholine (ACh) levels in the cerebral cortex of rats after i.p. administration of choline (100 mg/kg) or AGC-choline (equivalent dose) (5 rats per experiment, nmol/g. X ± MSE)

| Time | Choline | | AGC-choline | |
|---|---|---|---|---|
| | Ch | ACh | Ch | ACh |
| 24 h | 18,0 ± 1,1 | 17,7 ± 1,8 | 18,2 ± 0,9 | 15,8 ± 0,7 |

*$p < 0.05$
**$p < 0.01$
***$p < 0.001$ against respective time 0
¯$p < 0.05$
¯¯$p < 0.01$
¯¯¯$p < 0.001$ against choline 2. Effect of AGC-choline (compound VI) and Ch in the functioning of the memory in rats of advanced age.

The trial was carried out on F-344 rats of 25-27 months, which were subjected to a passive avoidance test. The duration of their retention was evaluated after a week of treatment with Ch (100 mg/kg), with pyracetam, a nootropic drug which influences passive avoidance (100 mg/kg), and with compound (VI) in a dose equivalent to 100 mg/kg of choline. Physiological solution was administered to a control group.

All treatments were conducted once a day for one week prior to the test.

As shown in Table 2, Ch and pyracetam increase the retention time to a statistically significant extent, but compound (VI) enables a retention time of more than double to be obtained.

These results demonstrate that compound (VI) possesses high activity in improving the functioning of the memory in animals of advanced age.

Because of the characteristics described under points 1. and 2., compound (VI) finds its most important therapeutic application in Alzheimer's disease.

TABLE 2

Retention time (seconds) for the passive avoidance test in Fisher 344 rats of advanced age treated for one week with choline (100 mg/kg) or pyracetam (100 mg/kg) or AGC-choline (choline equivalent to 100 mg/kg); n = 8 per group X ± MSE

| Physiological solution | Choline | Pyracetam | AGC-choline |
|---|---|---|---|
| 27,6 ± 4,3 | 42,5 ± 3,9* | 54,5 ± 5,1* | 156,3 ± 8,9***¯¯ |

*$p < 0.5$
***$p < 0.001$ against physiological solution
¯¯$p < 0.001$ against choline and pyracetam 3. Effect of AGC-GABOB (compound IX) on tardive dyskinesia induced by neuroleptics Stereotypy was evaluated in Sprague-Dawley rats of weight 220-270 g after injection with various doses of apomorphine (dopamine antagonist) following a period of 10 days of treatment with haloperidol (2 mg/kg i.p.) plus physiological solution or plus compound (IX) in a dose equivalent to 400 mg/kg of GABOB per day.

Three days after administration of the combined treatments, stereotypy produced by apomorphine was checked in the two groups of rats treated with haloperidol plus physiological solution and haloperidol plus compound (IX), compared with a group of rats treated only with physiological solution.

From Table 3 it can be seen that with three increasing doses of apomorphine (0.125, 0.25 and 0.5 mg/kg s.c.), in the rats which had undergone chronic treatment with haloperidol+physiological solution there is an increase in stereotypy which is about twice as high as in the untreated rats.

Treatment with compound (IX) prevents development of stereotypy, particularly at the higher apomorphine doses.

These results demonstrate that compound (IX) has strong GABAantagonist activity so that its use can be anticipated in various clinical conditions of receptor supersensitivity.

Compound (IX) is mostly indicated for tremor and spasticity conditions determined by brain degeneration syndromes.

TABLE 3

Cumulative stereotypy values for various doses of s.c.-administered apomorphine in rats 3 days after the end of 10 days of treatment with haloperidol (2 mg/kg i.p.) + physiological solution or + AGC-GABOB (400 mg/kg i.p.)

| | Apomorphine dose (mg/kg) | | |
|---|---|---|---|
| | 0.125 | 0.25 | 0.50 |
| | Stereotypy values | | |
| a) haloperidol + physiological solution | 15.2 ± 3.1 | 22.4 ± 2.7 | 31.8 ± 4.3 |
| b) haloperidol + AGC-GABOB | 11.2 ± 1.7**¯ | 14.4 ± 2.3***¯ | 18.1 ± 3.7*** |
| c) physiological solution | 7,2 ± 0,7 | 12,3 ± 1,9 | 18,7 ± 4,1 |

X ± SD, 8 rats per group
**$p < 0.01$
***$p < 0.001$ against group a
¯$p < 0.05$ against group c Other compounds of the invention were subjected to pharmacological trials to determine their activity.

From the results obtained, the following indications were found for the individual compounds.

Compound (I) where R is a glycine derivative: this is particularly indicated for reducing neuron hyperpolarization in spastic conditions or in Parkinson-like syndromes in degenerative diseases of the brain. The experimental data indicate a potent antagonist activity against muscular spasticity induced by strychnine.

Compound (I) where R is a glutamic acid derivative: this is useful in stimulating neuron sensitivity in various conditions.

Compound (I) where R is an Me-D-aspartate derivative: this is particularly indicated for cases of muscular hypotonia in degenerative diseases, and can also be used under conditions of areflexia determined by cerebral ischemia. The compound was evaluated for mice in muscular hypotonia induced by injecting d-amino-adipate, 2-amino-5-phosphovalerate.

Compound (I) where R is an L-pyroglutamyl-L-histidyl-L-choline derivative: this is an effective agent in the treatment of motoneuron syndromes. Patients affected by these syndromes suffer from spasticity, frequently associated with cerebral degeneration. Studies of the muscular condition in rodents intoxicated with nitrofurantoin showed that the compound has a potent long-lasting antispastic activity.

Compound (I) where R is a hydroxytryptophan derivative: this compound exercises a potent central activity against hemicrania and vertigo, and can be particularly useful in treating malfunctions of the autonomous nervous system in old people. The antivertigo activity was experimented in rodents by various behavioural tests.

Compound (I) where R is an MSH/ACTH derivative with the two components in the ratio of 4:10: this compound exercises a potent activity on attention and memory; in behavioural tests it produced a marked long-term increase in attention in mice and rats.

Compound (I) where R is an ACTH derivative: tests carried out on rodents showed that this compound strongly potentiates memory.

Compound (I) where R is a 1-desamino-8-D-argininevasopressin derivative: tests carried out on mice showed a marked prolongation in memory performance.

Compound (I) where R is an S-adenosylmethionine derivative: behavioural tests showed that this compound exercises an antidepressive activity which is longer lasting than S-adenosylmethionine, both under basal conditions and in the case of depression induced by reserpine.

From the aforegoing description it can be concluded that the compounds of formula (I) according to the present invention constitute a series of products effective for various neurological syndromes and particularly degenerative diseases of the brain, and for clinical syndromes which require treatment with psychoactive drugs.

Said compounds can be prepared in the form of pharmaceutical compositions for parenteral administration.

We claim:

1. Chemically and sterically pure synthetic amphiphilic glycoconjugates of the formula (I):

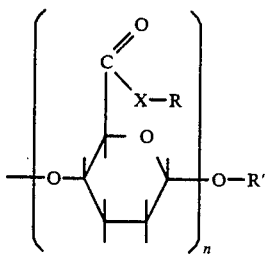

(I)

in which: the saccharide ring represents a monosaccharide;

X represents O or NH and, when X represents O, R is a choline radical whereas, when X represents NH, R is an amino acid or peptide radical selected from the group consisting of glycine, glutamic acid, Me-D-aspartate, L-pyroglutamyl-L-histidyl-L-proline, γ-amino-β-hydroxy butyric acid, hydroxytryptophan, Melanocyte Stimulating Hormone/Adrenocorticotropic Hormone, Adrenocorticotropic Hormone, 1-desamino-8-D-argininevasopressin and S-adenosyl-methionine; R' represents functional group selected from the group consisting of a saturated, linear $C_8$–$C_{18}$ aliphatic chain, an unsaturated linear $C_8$–$C_{18}$ aliphatic chain, branched $C_8$–$C_{18}$ aliphatic chain, a

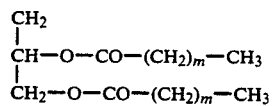

group and a

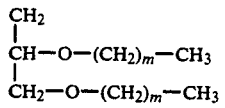

group where m is between 7 and 17; and n is a whole number from 1 to 5.

2. Glycoconjugates as claimed in claim 1, wherein R is a glycine radical.

3. Glycoconjugates as claimed in claim 1, wherein R is a glutamic acid radical.

4. Glycoconjugates as claimed in claim 1, wherein R is a Me-D-aspartate radical.

5. Glycoconjugates as claimed in claim 1, wherein R is a L-pyroglutamyl-L-histidyl-L-proline radical.

6. Glycoconjugates as claimed in claim 1, wherein R is a γ-amino-β-hydroxybutyric acid (GABOB) radical.

7. Glycoconjugates as claimed in claim 1, wherein R is a hydroxytryptophan radical.

8. Glycoconjugates as claimed in claim 1, wherein R is a MSH/ACTH (melanocyte stimulating hormone/adrenocorticotropin).

9. Glycoconjugates as claimed in claim 1, wherein R is a group derived from ACTH (adrenocorticotropin).

10. Glycoconjugates as claimed in claim 1, wherein R is a 1-desamino-8-D-argininevasopressin radical.

11. Glycoconjugates as claimed in claim 1, wherein R is a S-adenosylmethionine radical.

* * * * *